United States Patent [19]

Seres et al.

[11] 4,353,734
[45] Oct. 12, 1982

[54] MALEIMIDE AND SUCCINIMIDE DERIVATIVES AND HERBICIDAL METHOD OF USE THEREOF

[75] Inventors: Jenö Seres, Istvánné Daróczí, nee Esuka; Jánosné Várkonyi, nee Slovicsko; Gabor Horvath, all of Budapest; Ildikó Szilágyi, Ocsa; Belane Radvanyi, nee Hegedüs, Budapest, all of Hungary

[73] Assignee: Chinoin Gyogyszer es Vegyeszeti Termekek Gyara R.T., Budapest, Hungary

[21] Appl. No.: 927,343

[22] Filed: Jul. 24, 1978

[30] Foreign Application Priority Data

Jul. 25, 1977 [HU] Hungary .................................. 1757

[51] Int. Cl.³ .................... A01N 43/36; C07D 207/40
[52] U.S. Cl. ...................................... 71/95; 260/326.5 FM
[58] Field of Search ..................... 260/326.4, 326.5 S, 260/326.5 FM, 326.5 E; 424/274; 71/95

[56] References Cited

U.S. PATENT DOCUMENTS 3,882,145  5/1975  Bissinger .......................... 260/326.4

OTHER PUBLICATIONS

Umio, Sumonori, Chemical Abstracts, vol. 72, 43221b, (1970).

*Primary Examiner*—David B. Springer
*Attorney, Agent, or Firm*—Karl F. Ross

[57] ABSTRACT

Compounds of the formulae

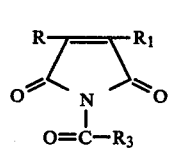 and 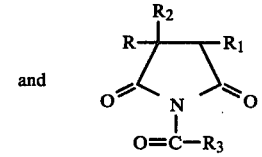

are disclosed wherein

R is hydrogen, halogen, phenyl, phenyl-$C_1$ to $C_4$ alkylthio, $C_1$ to $C_6$ alkylthio, $C_5$ to $C_7$ cycloalkylthio, phenylthio or phenylsulfonyl;

$R_1$ is amino, $C_5$ to $C_7$ cycloalkylamino, $C_1$ to $C_6$ alkylamino, $C_1$ to $C_4$-alkoxy-substituted-phenyl-($C_1$ to $C_4$-alkylamino), phenylamino, naphthylamino, furfurylamino, phenyl-($C_1$ to $C_4$)-alkylamino, phenylamino-substituted by $C_1$ to $C_4$ alkoxy, halogen or $C_1$ to $C_4$ alkyl or phenylsulfonyl.

$R_2$ is hydrogen; and $R_3$ is $C_1$ to $C_6$ alkyl, alkoxy or phenyl. The compounds have herbicidal properties.

8 Claims, No Drawings

MALEIMIDE AND SUCCINIMIDE DERIVATIVES AND HERBICIDAL METHOD OF USE THEREOF

The present invention is directed to new maleinimides and succinimides of the formulae

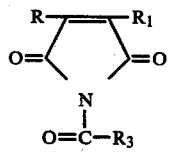
I and

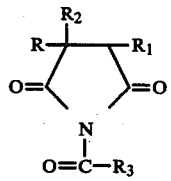
II wherein

R represents hydrogen or halogen, hydroxy or substituted hydroxy, mercapto, substituted mercapto, alkyl, cycloalkyl, aryl, aralkyl, or a heterocyclic radical or an alkyl group substituted with a heterocyclic group, or substituted sulfonyl, $R_1$ is hydrogen, alkyl, aryl, aralkyl, amino or substituted amino or a heterocyclic group or alkyl substituted with a heterocyclic group, $R_2$ is hydrogen or halogen, alkyl, aryl, aralkyl, or substituted amino, $R_3$ represents hydrogen, alkyl, aryl, aralkyl, alkoxy, aryloxy or a heterocyclic radical.

The invention also provides a process for the preparation of the compounds of the formula I or II and herbicidally active compositions consisting of compounds of the formula I or II as active ingredients.

The term substituted hydroxyl and mercapto in the definition of R as used hereinafter stands for alkyl-, aryl- or aralkyl-substituted hydroxy and mercapto.

The alkyl group stands for $C_{1-20}$ straight or branched alkyl, preferably $C_{1-6}$, particularly $C_{1-4}$ alkyl, such as methyl, ethyl, n- and isopropyl, n, iso, sec. and tertiary butyl, pentyl or hexyl. The cycloalkyl groups contains 4 to 8, preferably 5 to 7 carbon atoms.

The aryl groups can be carbocyclic or heterocyclic and may contain 6 to 10 cyclic carbon atoms or carbon and heteroatoms and can be unsubstituted or substituted. The aryl groups can be substituted by one or several alkyl, alkoxy groups or halogen.

The aralkyl groups may consist of an aryl and alkyl group as defined above.

Halogen stands for fluorine, chlorine, bromine and iodine, preferably for chlorine and bromine.

As heterocyclic groups groups containing 5 to 8 cyclic atoms are preferred. The heterocyclic groups preferably contain as heteroatoms one or more nitrogen, sulfur and/or oxygen atoms.

Compounds of the formulae I and II of the invention are particularly preferred if R represents hydrogen, or halogen, preferably chlorine, phenyl, phenyl-$C_{1-4}$-alkylthio, phenylthio, $C_{1-6}$-alkylthio, $C_{5-7}$ cycloalkylthio, or phenylsulfonyl, $R_1$ represents hydrogen, amino, $C_{5-7}$ cycloalkylamino, $C_{1-6}$ alkylamino, $C_{1-4}$ alkoxy-substituted phenyl-$C_{1-4}$-alkylamino, phenylamino, naphthylamino, furfurylamino, phenyl-$C_{1-4}$ alkylamino, phenylamino substituted by a group selected from halogen, $C_{1-4}$ alkyl, and $C_{1-4}$ alkoxy $R_2$ is hydrogen $R_3$ represents $C_{1-6}$ alkyl, alkoxy or phenyl.

The herbicide compositions of the invention may contain in addition to the active ingredients, usually employed diluents, surfactants and/or other formulation excipients.

The diluents may be used in solid and/or liquid state, and include synthetic or natural stone grist, clays, inert organic solvents, such as mineral oil fractions, alcohols, ketones, water or various ionic or non-ionic surface active agents. The formulations may also contain adherence increasing agents. The formulations contain 0,1 to 99% by weight active ingredient(s).

Similar N-acylated derivatives of unsubstituted succinimide and maleinimide derivatives are disclosed. N-Carbethoxy-succinimide for example, was prepared from the potassium salt of succinimide and ethylchloroformate in benzene Ber. 54, 1114 (1921). N-Acetyl-succinimide has been prepared from succinimide by boiling it with acetic acid anhydride (Ber. 33, 2225 (19)).

N-Benzoyl-succinimide was prepared by boiling a solution of succinimide with benzoyl chloride in pyridine (J. Chem. Soc., 85, 1685). N-Acetyl-maleinimide was prepared by oxidizing N-acetylpyrrole with chromotrioxide (Zhur, Obsch. Khim., 19, 2118-22 (1949)).

The preparation of the maleinimide derivatives which are the closest to the compounds of the invention has been disclosed in C.A. 72, 43221 b), 3-chloro-4-aryl-substituted succinimides are acetylated with acetic acid anhydride on nitrogen under boiling and hydrochloric acid is split off giving the corresponding 3-aryl-4-acetylated maleinimides.

According to the present invention compounds of the formulae I and II are prepared by (a) reacting compounds of the formula

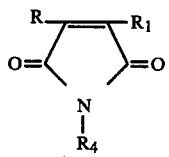
III wherein $R_4$ is hydrogen or alkali metal—with compounds of the formula

$R_3$—COX
V wherein X is halogen-in order to prepare compounds of the formula I, or (b) reacting compounds of the formula III with the compounds of the formula

$(R_3CO)_2O$
VI in order to obtain compounds of the formula I, or (c) reacting compounds of the formula

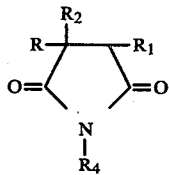

IV with the compounds of the formula V in order to obtain compounds of the formula II or (d) reacting compounds of the formula IV with the compounds of the formula VI in order to obtain compounds of the formula II.

The reactions according to methods (a), (b), (c) and (d) may be carried out in the presence of a solvent, preferably acetone, or without employing a solvent, by adding acid binding agents, preferably triethylamine or without.

Compounds of the invention of the formulae I and II display a valuable herbicidal activity and may thus be employed as active ingredients of agrochemical compositions.

Compounds of the formulae I and II may preferably be prepared by dissolving or suspending substituted maleinor succinimides of the formulae III or IV contained hydrogen on the nitrogen atom in an inert solvent, such as acetone, benzene, toluene or dioxan and reacting the thus obtained mixture with an equivalent amount or 1.5 equivalents of acylating agent. The reaction is carried out at room temperature or under the boiling of the reaction mixture by adding triethylamine or anothers acid binding agent in an amount which is equivalent to the amount of the acylating agent or without any acid binding agent.

It is particularly advantageous if the acylation is conducted in acetone by adding the acylating agent simultaneously with the acid binding agent at 25° C. The reaction mixture is stirred at room temperature for 1 hour and boiled for a further 10–30 minutes.

The reaction mixture is further processed according to the properties of the acylated substance.

If the acylated compound of the formula I or II is precipitated from the reaction mixture, the crude product is obtained after filtration and washed with water and the end product is obtained by crystallization.

If the acylated product of the formula I or II does not precipitate from the reaction mixture, the formed and precipitated by-product is filtered off and/or filtered after concentration and the crude product is separated by evaporation and the pure end product is obtained by crystallization as described above.

The compounds of the invention of the formula I and II may be formulated and the formulation show herbicidal activity. The substances may be further used without formulation as intermediate products in the synthesis of further compounds.

The advantage of the process of the invention is in giving a simple direct method for the preparation of the compounds of the formulae I and II, which offers pure end products suitable for further use.

The compounds of the formulae III and IV used as starting materials may be prepared by methods known per se. 3-Bromo-maleinimide and the appropriate amines were reacted in order to obtain 3-substituted amino derivatives (Ber., 21, 2718/1888/, Gazz. Chim. Ital. 65, 1221 (1935)). The 3,4-disubstituted maleinimides were prepared according to Tetrahedron 24, 4051 (1968), J. Org. Chem. 26, 2032 (1961), J. Amer. Soc. Chem., 80, 1385 (1958). The 3-substituted succinimides were prepared according to J. Org. Chem., 26, 787 (1961).

The further details of the invention are illustrated by the following Examples without limiting the scope of the invention to the Examples.

EXAMPLE 1

7.52 g. (0.04 mole) of 3-phenylamino-maleinimide are dissolved in 280 ml. of acetone under stirring, 6.48 g. (0.06 mole) of ethylchloroformate and 6.06 g. (0.06 mole) of triethylamine are added dropwise simultaneously under stirring. The temperature of the mixture is maintained at 25°–30° C. during the addition of the above substances. The mixture is then stirred for 1.5 hours at room temperature and heated under reflux for 10 minutes. The mixture is then allowed to stand overnight and the precipitated triethylamine-chlorohydrate is filtered off. The mother liquor containing acetone is evaporated to dryness. The obtained yellow crystalline substance is washed with 2×15 ml. of water and filtered off. After drying the crude 3-phenylamino-N-carbethoxy-maleinimide may be, if desired, recrystallized from ethyl acetate or absolute alcohol.

Yield: 7.6 g., (73%), m.p.: 168°–172° C.

EXAMPLE 2

1.88 g. (0.01 mole) of 3-phenylamino-maleinimide are dissolved in 70 ml. of acetone. To this mixture 1.17 g. (0.015 mole) of acetylchloride and 1.51 g. (0.015 mole) of triethylamine are added dropwise under stirring. In the course of the addition the temperature of the reaction mixture is maintained at 25°–35° C. The reaction mixture is then stirred for 2.5 hours at room temperature and heated for 1.5 hours and allowed to stand at room temperature overnight. The product is precipitated together with triethylamine-chlorohydrate. The crystalline mixture is filtered and washed with 2×5 ml. of water. The yellow crystalline substance is recrystallized after drying from acetone or dioxan. 3-Phenylamino-N-acetyl-maleinimide is obtained.

Yield: 0.85 g. (36.9%); m.p.: 217°–219° C.

EXAMPLE 3

3.76 g. (0.02 mole) of 3-phenylamino-maleinimide are dissolved under heating in 60 ml. of acetic acid anhydride. The solution is heated under reflux for 5 hours and allowed to stand overnight. The precipitated pale yellow crystals are filtered and washed with 3×10 ml. of water. The obtained 3-phenylamino-N-acetylmaleinimide is, if desired, recrystallized after drying from acetone or dioxan.

Yield: 4 g. (86%); m.p.: 218°–219° C.

EXAMPLE 4

1.88 g. (0.01 mole) of 3-phenylamino-maleinimide are dissolved in 70 ml. of acetone under stirring. To this mixture 2.1 g. (0.015 mole) of benzoyl chloride and 1.51 g. (0.015 mole) of triethylamine are added dropwise under simultaneous stirring. The temperature is maintained at 25°–30° C. during the addition. The mixture is then stirred for 2.5 hours at room temperature and heated for 1.5 hours. The mixture is allowed to stand overnight. The product is precipitating together with triethylaminechlorohydrate. The crystalline mixture is filtered and washed with 2×10 ml. of water. After drying a yellow crystalline product is obtained, which can be recrystallized from chloroform or acetone, if desired. 3-Phenylamino-N-benzoyl-maleinimide is obtained.

Yield: 1.24 g. (42.4%); m.p.: 238°–41° C.

EXAMPLE 5

4.44 g. (0.15 mole) of 3-phenylamino-4-phenylthiomaleinimide are dissolved in 60 ml. of acetone under stirring. To the mixture cooled with icy water there is added a mixture of 1.95 ml. (0.025 moles) of methylchloroformate and 2.25 ml. (0.016 mole) of triethylamine under stirring. The mixture is then stirred for another 3 hours under cooling with icy water. The precipitated triethylamine chlorohydrate is filtered off. The mother liquor containing acetone is evaporated to dryness. The thus obtained orange crystals are washed with 3×5 ml. of petrolether. After drying the obtained 3-phenylamino-4-phenylthio-N-carbomethoxy-maleinimide is optionally recrystallized from methanol.

Yield: 4.55 g. (85%); m.p.: 156°–157° C.

EXAMPLE 6

18.9 g. (0.1 mole) of 3-phenyl-3-methyl-succinimide are dissolved under stirring in 100 ml. of acetone. To this mixture 16.2 g. (0.15 mole) of ethylchloroformate and 15.1 g. (0.15 mole) of triethylamine are added dropwise under stirring. The temperature of the mixture is maintained at 25°–30° C. during the addition. The mixture is then stirred at room temperature and heated under reflux for 10 minutes. The mixture is allowed to stand overnight and the precipitated triethyl amine is filtered off. The mother liquor containing acetone is evaporated to dryness. The residual oil is precipitated on cooling. The obtained almost white crystalline substance is washed with water and filtered off. After drying the obtained 3-phenyl-3-methyl-N-carbethoxy-succinimide is optionally recrystallized from 96% alcohol.

Yield: 13.75 g. (52%); m.p.: 32°–34° C.

The following compounds of the general formula

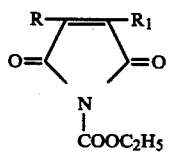

VII of the Table 1 are prepared according to Example 1 from the corresponding substituted maleinimides of the general formula III.

TABLE 1

| No of Example | R | $R_1$ | Yield % | m.p.: °C. |
|---|---|---|---|---|
| 7. | hydrogen | 4-methyl-phenylamino- | 85.7 | 186–89 |
| 8. | hydrogen | 4-methoxy-phenylamino- | 70 | 166–69 |
| 9. | hydrogen | 4-chloro-phenylamino- | 63 | 230–248 |
| 10. | hydrogen | 4-bromo-phenylamino- | 78 | 240–45 |
| 11. | hydrogen | benzylamino- | 68.4 | 86–90 |
| 12. | hydrogen | 2-(3,4-dimethoxy-phenyl)-ethylamino- | 68.9 | 108–112 |
| 13. | hydrogen | n-butylamino- | 90 | 77–80 |
| 14. | hydrogen | cyclohexylamino- | 92 | 92–96 |
| 15. | chlorine | amino- | 80 | 174–80 |
| 16. | chlorine | phenylamino- | 84 | 120–26 |
| 17. | chlorine | 4-methyl-phenylamino- | 81 | 135–40 |

TABLE 1-continued

| No of Example | R | $R_1$ | Yield % | m.p.: °C. |
|---|---|---|---|---|
| 18. | chlorine | 4-methoxy-phenylamino- | 84.3 | 158–163 |
| 19. | chlorine | 4-chloro-phenylamino- | 76.8 | 190–99 |
| 20. | chlorine | 3-chloro-phenylamino | 53.6 | 150–161 |
| 21. | chlorine | 3,5-dichloro-phenylamino- | 89 | 200–207 |
| 22. | chlorine | 4-bromo-phenylamino- | 87 | 190–98 |
| 23. | chlorine | 2-naphthylamino- | 74 | 170–75 |
| 24. | phenyl- | phenylamino- | 83 | 132–34 |
| 25. | phenyl-thio- | phenylamino- | 85.6 | 133–35 |
| 26. | phenyl-sulfonyl- | phenylamino- | 72.5 | 205–206 |
| 27. | hydrogen | n-hexylamino- | 67 | 56–59 |
| 28. | chlorine | 2-methyl-phenylamino- | 85 | 116–19 |
| 29. | phenyl- | benzylamino- | 73 | 109–111 |
| 30. | phenyl- | n-hexylamino- | 80 | 46–47 |
| 31. | phenyl- | octylamino- | 81 | 68–70 |
| 32. | phenyl- | cyclohexylamino- | 84 | 87–89 |
| 33. | phenyl | n-butylamino- | 83 | 63–64 |
| 34. | hydrogen | furfurylamino- | 95 | 79–83 |
| 35. | cyclohexylthio- | phenylamino- | 88 | 114–16 |
| 36. | benzylthio- | phenylamino- | 89 | 107–108 |
| 37. | i-butylthio- | phenylamino | 89 | 86–88 |
| 38. | ethylthio- | phenylamino- | 90 | 70–71 |
| 39. | 4-methyl-phenyl-sulfonyl- | phenylamino- | 58 | 182–84 |

The following compounds are also prepared according to Example 1.:

40. 3-phenylamino-4-(iso-butylthio)-N-carbomethoxy-maleinimide, m.p.: 113°–115° C.,
41. 3-phenylamino-4-ethylthio-N-carbomethoxy-maleinimide, m.p.: 83°–86° C.,
42. 3-phenylamino-4-benzylthio-N-carbomethoxy-maleinimide, m.p.: 150°–151° C.,
43. 3-phenylamino-4-cyclohexylthio-N-carbomethoxy-maleinimide, m.p.: 131°–134° C.,
44. 3-phenylamino-4-chloro-N-carbomethoxymaleinimide, m.p.: 155°–157° C.

The following compounds of the formula

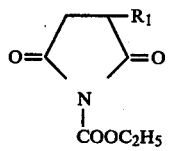

VIII may be prepared according to Example 6 from substituted succinimides of the formula IV

TABLE 2

| No. of Example | R | Yield % | M.p.: °C. |
|---|---|---|---|
| 45. | phenylamino- | 67 | 102–105 |
| 46. | 4-methyl-phenylamino- | 58.8 | 94–99 |
| 47. | 4-chloro-phenylamino- | 89 | 130–33 |

The herbicidal activity of compounds of the invention of the general formulae I and II is shown by the following tests.

EXAMPLE A

Germination Test

The germination inhibiting activity was tested on white mustard (*Sinapis alba*) and Hungarian grass (*Setaria* sp.) as test-plants. The test-compound was administered at a dose of 10 mg. (Petri-plate) and the germination was carried out for 1 week in dark and the inhibition was determined in % related to the untreated control. The obtained results are summarized in Table 3.

EXAMPLE B

Preemergence Treatment

Mustard and Hungarian grass seeds were sown to culture plates. After sowing 20 kg./ha. active ingredient were applied to the soil and the culture plate was put in a greenhouse for 1 week. The herbicidal activity was evaluated after 1 week and it was determined in % related to the untreated control. The obtained results are to be found in Table 3.

EXAMPLE C

Postemergence Treatment

The foliage of one week old mustard and Hungarian grass plants was sprayed with a liquid containing active ingredient of the test compound in an amount corresponding to 20 kg./ha. The herbicidal activity was determined one week after the treatment and expressed in % of the untreated controls. The obtained results are shown in Table 3.

TABLE 3

| Code No. of active ingredient | Germination inhibition | | Preemergence activity % | | Postemergence activity % | |
|---|---|---|---|---|---|---|
| | Setaria | Sinapis | Setaria | Sinapis | Setaria | Sinapis |
| 971 | 82 | 75 | — | — | 90 | 45 |
| 1144 | 41 | 76 | 10 | 10 | 10 | 45 |
| 1223 | 97 | 90 | 18 | 20 | 0 | 30 |
| 1225 | 80 | 80 | 18 | 12 | 0 | 45 |
| 1227 | 40 | 70 | 20 | 18 | 10 | 20 |
| 1243 | 95 | 95 | — | — | 60 | 65 |
| 1271 | 10 | 10 | — | — | — | — |
| 1272 | 10 | 15 | — | — | — | — |
| 1473 | — | — | — | — | 0 | 0 |
| 1524 | 0 | 0 | 18 | 20 | 0 | 0 |
| 1527 | 10 | 12 | 12 | 16 | 0 | 0 |
| 1528 | 0 | 0 | 20 | 15 | 0 | 0 |
| 1532 | 0 | 0 | — | — | 0 | 0 |
| 1539 | 10 | 15 | — | — | 0 | 0 |
| 1541 | 0 | 0 | — | — | 0 | 0 |
| 1542 | 16 | 13 | — | — | 0 | 0 |
| 1622 | 0 | 0 | — | — | 0 | 0 |
| 1662 | 0 | 0 | — | — | 0 | 0 |
| 1667 | 15 | 20 | — | — | 0 | 0 |
| 1668 | 0 | 0 | — | — | 0 | 0 |
| 1670 | 0 | 0 | — | — | 0 | 0 |
| 1673 | 0 | 0 | — | — | 0 | 0 |

The following compounds have been assigned the individual code numbers given.

| Code Number | Compound |
|---|---|
| 971 | 3-phenylamino-N—carbethoxy-maleinimide |
| 1144 | 3-cyclohexylamino-N—carbethoxy-maleinimide |
| 1223 | 3-phenylamino-4-chloro-N—carbethoxy-maleinimide |
| 1225 | 3-(4-methyl-phenylamino)-4-chloro-N—carbethoxy-maleinimide |
| 1227 | 3-(4-methoxy-phenylamino)-4-chloro-N—carbethoxy-maleinimide |
| 1243 | 3-amino-4-chloro-N—carbethoxy-maleinimide |
| 1271 | 3-(4-chloro-phenylamino)-4-chloro-N—carbethoxy-maleinimide |
| 1272 | 3-(3,5-dichloro-phenylamino)-4-chloro-N—carbethoxy-maleinimide |
| 1473 | 3-phenylsulfonyl-N—carbethoxy-maleinimide |
| 1524 | 3-n-butylamino-N—carbethoxy-maleinimide |
| 1527 | 3-phenylamino-N—carbethoxy-succinimide |
| 1528 | 3-(3,4-dimethoxy-phenyl-ethylamino)-N—carbethoxy-maleinimide |
| 1532 | 3-(β-naphthylamino)-4-chloro-N—carbethoxy-maleinimide |
| 1539 | 3-(4-methyl-phenylamino)-N—carbethoxy-succinimide |
| 1541 | 3-(4-chloro-phenylamino)-N—carbethoxy-succinimide |
| 1542 | 3-(n-hexylamino)-N—carbethoxy-maleinimide |
| 1622 | 3-phenylamino-4-phenylthio-N—carbethoxy-maleinimide |
| 1662 | 3-phenylamino-4-phenylsulfonyl-N—carbethoxy-maleinimide |
| 1667 | 3-phenylamino-4-(i-butylthio)-N—carbethoxy-maleinimide |
| 1668 | 3-phenylamino-4-(i-butylthio)-N—carbmethoxy-maleinimide |
| 1670 | 3-phenylamino-4-benzylthio-N—carbethoxy-maleinimide |
| 1673 | 3-phenylamino-4-cyclohexylthio-N—carbethoxy-maleinimide |

What we claim is:

1. A compound of the formula

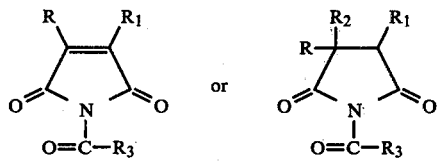

wherein

R is hydrogen, halogen, phenyl, phenyl-$C_1$ to $C_4$ alkylthio, $C_1$ to $C_6$ alkylthio, $C_5$ to $C_7$ cycloalkylthio, phenylthio or phenylsulfonyl;

$R_1$ is amino, $C_5$ to $C_7$ cycloalkylamino, $C_1$ to $C_6$ alkylamino, $C_1$ to $C_4$-alkoxy-substituted-phenyl-($C_1$ to $C_4$-alkylamino), phenylamino, naphthylamino, furfurylamino, phenyl-($C_1$ to $C_4$)alkylamino, phenylamino-substituted by $C_1$ to $C_4$ alkoxy, halogen or $C_1$ to $C_4$ alkyl or phenylsulfonyl;

$R_2$ is hydrogen; and $R_3$ is $C_1$ to $C_6$ alkyl, alkoxy or phenyl.

2. A compound as defined in claim 1 and selected from the group which consists of:
   3-phenylamino-N-carbethoxy-maleimide,
   3-phenylamino-N-acetyl-maleimide,
   3-phenylamino-N-benzoyl-maleimide,
   3-phenylamino-4-phenylthio-N-carbomethoxy-maleimide,
   3-(4-methyl-phenylamino)-N-carbethoxy-maleimide,
   3-(4-methoxy-phenylamino)-N-carbethoxy-maleimide,
   3-(4-chlorophenylamino)-N-carbethoxy-maleimide,
   3-benzylamino-N-carbethoxy-maleimide,
   3-[2-(3,4-dimethoxyphenyl)-ethylamino]-N-carbethoxy-maleimide,
   3-(n-butylamino)-N-carbethoxy-maleimide,
   3-cyclohexylamino-N-carbethoxy-maleimide,
   3-amino-4-chloro-N-carbethoxy-maleimide,
   3-(4-methyl-phenylamino)-4-chloro-N-carbethoxy-maleimide, 3-(4-methoxy-phenylamino)-4-chloro-N-carbethoxy-maleimide,
3-(4-chlorophenylamino)-4-chloro-N-carbethoxy-maleimide,
3-(3-chlorophenylamino)-4-chloro-N-carbethoxy-maleimide,
3-(3,4-dichlorophenylamino)-4-chloro-N-carbethoxy-maleimide,
3-(4-bromophenylamino)-4-chloro-N-carbethoxy-maleimide,
3-(2-naphthylamino)-4-chloro-N-carbethoxy-maleimide,
3-phenylamino-4-phenyl-N-carbethoxy-maleimide,
3-phenylamino-4-phenylthio-N-carbethoxy-maleimide,
3-phenylamino-4-phenylsulfonyl-N-carbethoxy-maleimide,
3-(n-hexylamino)-N-carbethoxy-maleimide,
3-(2-methyl-phenylamino)-4-chloro-N-carbethoxy-maleimide,
3-benzylamino-4-phenyl-N-carbethoxy-maleimide,
3-(n-hexylamino)-4-phenyl-carbethoxy-maleimide,
3-octylamino-4-phenyl-N-carbethoxy-maleimide,
3-cyclohexylamino-4-phenyl-N-carbethoxy-maleimide,
3-(n-butylamino)-4-phenyl-N-carbethoxy-maleimide,
3-furfurylamino-N-carbethoxy-maleimide,
3-phenylamino-4-cyclohexylthio-N-carbethoxy-maleimide,
3-phenylamino-4-benzylthio-N-carbethoxy-maleimide,
3-phenylamino-4-(i-butylthio)-N-carbethoxy-maleimide,
3-phenylamino-4-ethylthio-N-carbethoxy-maleimide,
3-phenylamino-N-(4-methyl-phenylsulfonyl)-N-carbethoxy-maleimide,
3-phenylamino-4-(i-butylthio)-N-carbomethoxy-maleimide,
3-phenylamino-4-ethylthio-N-carbomethoxy-maleimide,
3-phenylamino-4-benzylthio-N-carbomethoxy-maleimide,
3-phenylamino-4-cyclohexylthio-N-carbomethoxy-maleimide,
3-phenylamino-4-chloro-N-carbomethoxy-maleimide,
3-phenylamino-4-chloro-N-carbethoxy-maleimide,
3-(3,5-dichlorophenylamino)-4-chloro-N-carbethoxy-maleimide,
3-phenylsulfonyl-N-carbethoxy-maleimide,
3-phenyl-3-methyl-N-carbethoxy-succinimide,
3-phenylamino-N-carbethoxy-succinimide,
3-(4-methyl-phenylamino)-N-carbethoxy-succinimide, and
3-(4-chlorophenylamino)-N-carbethoxy-succinimide.

3. The compound defined in claim 1 which is 3-phenylamino-N-carbethoxy-maleimide.

4. A compound of the formula

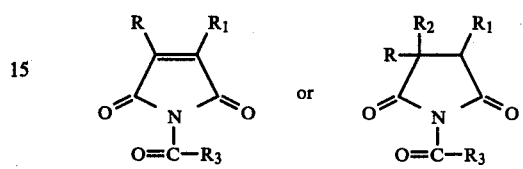

wherein
R is hydrogen, halogen, phenyl, phenyl-$C_1$ to $C_4$ alkylthio, $C_1$ to $C_6$ alkylthio, $C_5$ to $C_7$ cycloalkylthio, phenylthio or phenylsulfonyl;
$R_1$ is amino, $C_5$ to $C_7$ cycloalkylamino, $C_1$ to $C_6$ alkylamino, $C_1$ to $C_4$-alkoxy-substituted-phenyl-($C_1$ to $C_4$-alkylamino), phenylamino, naphthylamino, furfurylamino, phenyl-($C_1$ to $C_4$)-alkylamino or phenylamino-substituted by $C_1$ to $C_4$ alkoxy, halogen or $C_1$ to $C_4$ alkyl;
$R_2$ is hydrogen; and
$R_3$ is $C_1$ to $C_6$ alkyl, alkoxy or phenyl.

5. An herbicide composition containing as an active ingredient, at least one compound as defined in claim 1 and an inert, solid or liquid diluent, surface active agents and/or other herbicidally effective formulation excipient.

6. The composition defined in claim 5 wherein said active ingredient is a compound as defined in claim 2.

7. A method of controlling undesirable vegetation comprising applying to the locus of such undesirable vegetation a herbicidally effective amount of a compound as defined in claim 1

8. A method of controlling undesirable vegetation comprising applying to the locus of such undesirable vegetation a herbicidally effective amount of at least one compound as defined in claim 2.

* * * * *